(12) United States Patent
Rehe

(10) Patent No.: US 9,398,840 B2
(45) Date of Patent: Jul. 26, 2016

(54) ENDOSCOPE WITH VARIABLE DIRECTION OF VIEW

(75) Inventor: Oliver Rehe, Tuttlingen (DE)

(73) Assignee: Henke-Sass, Wolf GmbH, Tuttlingen (DE)

(*) Notice: Subject to any disclaimer, the term of this patent is extended or adjusted under 35 U.S.C. 154(b) by 849 days.

(21) Appl. No.: 13/450,712

(22) Filed: Apr. 19, 2012

(65) Prior Publication Data

US 2012/0271112 A1 Oct. 25, 2012

(30) Foreign Application Priority Data

Apr. 20, 2011 (DE) .................. 10 2011 007 797

(51) Int. Cl.
| | | |
|---|---|---|
| A61B 1/06 | (2006.01) | |
| A61B 1/00 | (2006.01) | |
| A61B 1/002 | (2006.01) | |
| A61B 1/04 | (2006.01) | |
| A61B 1/055 | (2006.01) | |

(52) U.S. Cl.
CPC ............ *A61B 1/00183* (2013.01); *A61B 1/002* (2013.01); *A61B 1/042* (2013.01); *A61B 1/055* (2013.01)

(58) Field of Classification Search
CPC .................. A61B 1/00172; A61B 1/00183
USPC .................. 600/173, 176, 167, 168, 170
See application file for complete search history.

(56) References Cited

U.S. PATENT DOCUMENTS

| | | | | |
|---|---|---|---|---|
| 5,359,453 | A | * | 10/1994 | Ning .............................. 359/435 |
| 5,683,348 | A | * | 11/1997 | Diener .......................... 600/143 |
| 6,306,082 | B1 | | 10/2001 | Takahashi et al. |
| 6,540,668 | B1 | | 4/2003 | Schulz et al. |
| 6,638,216 | B1 | * | 10/2003 | Durell ............................. 600/173 |
| 2002/0082476 | A1 | | 6/2002 | Takahashi et al. |
| 2010/0195007 | A1 | | 8/2010 | Takahashi |

FOREIGN PATENT DOCUMENTS

| | | |
|---|---|---|
| DE | 4304422 C1 | 7/1994 |
| DE | 195 09 885 A1 | 9/1995 |
| JP | 09248276 A | 9/1997 |

OTHER PUBLICATIONS

English translation of search report by the German patent and Trademark Office for the priority application (No. 102011007797.9), report issued Jan. 23, 2012, 5 pages.

* cited by examiner

*Primary Examiner* — Matthew J Kasztejna
*Assistant Examiner* — Rynae Boler
(74) *Attorney, Agent, or Firm* — Skaar Ulbrich Macari, P.A.

(57) ABSTRACT

An endoscope with a variable direction of view is provided, which includes an endoscope shaft and imaging optics arranged inside the endoscope shaft. These image an object located before the distal end of the endoscope and produce an image of the object in the proximal area of the endoscope in which a field stop is arranged. The produced image is larger than the field stop. In the proximal area of the endoscope an image module is arranged with which the relative position between the produced image and the field stop can be changed for changing the section of the produced image visible after the field stop in order to change the direction of view of the endoscope.

10 Claims, 4 Drawing Sheets

ENDOSCOPE WITH VARIABLE DIRECTION OF VIEW

PRIORITY

The present application claims priority to German Application No. 102011007797.9, filed Apr. 20, 2011, which is hereby incorporated by reference in its entirety.

FIELD

The present invention relates to an endoscope with a variable direction of view.

BACKGROUND

Endoscopes with a variable direction of view frequently have in the distal end of the endoscope a swivellable mirror or a swivellable prism in order to change the direction of view. The provision of the swivellable mirror or the swivellable prism in the distal end of the endoscope necessitates an increased mechanical outlay. Also there must always still be sufficient space for the swiveling and the whole endoscope, including the swiveling mechanism, must still be producible per se, which sets limits on miniaturization.

Furthermore it is also possible to form the endoscope such that the whole endoscope tip can be bent out in order to change the direction of view. In this case there is either a flexible image conductor or an image sensor built into the tip of the endoscope. However, such endoscopes are mostly very sensitive because of the necessary flexible bush for the tip of the endoscope, can be produced in an autoclavable version only with great difficulty and are very repair-prone.

SUMMARY

It is an object of the invention to make available an endoscope with a variable direction of view with which the disadvantages named at the outset can be overcome as completely as possible.

The object is achieved according to certain embodiments of the invention in an endoscope of the type named at the outset by having the produced image larger than the field stop and arranging in the proximal area of the endoscope an image module with which the relative position between the produced image and the field stop can be changed for changing the section of the produced image visible after the field stop in order to change the direction of view of the endoscope.

With the endoscope according to certain embodiments of the invention the change of direction of view is thus brought about by a relative change of position of the produced image and of the field stop in the proximal area of the endoscope, whereby advantageously no moving optical element need be provided at the distal end of the endoscope. A further miniaturization of the endoscope and in particular of the endoscope shaft can thereby be carried out. Furthermore producibility can be ensured, as no moving optical elements are to be arranged in the distal end of the endoscope. The endoscope can also be formed easily autoclavable because the endoscope shaft as such can be formed as a rigid endoscope shaft.

The endoscope according to certain embodiments of the invention is in particular formed such that a continuous or stepless change of the relative position between the produced image and the field stop is possible by means of the image module or is brought about by same. A continuous change of the direction of view is thereby brought about. Therefore, this could also be called a "scanning" endoscope.

By a continuous or stepless change is meant in particular here also a quasi-continuous change due to a mechanically dictated minimum increment which, however, preferably is as small as possible.

The imaging optics preferably produce a single image of the object, wherein the single image is coherent or continuous. The image is thus exclusively the imaging of the object in a continuous image angular range.

With the endoscope according to certain embodiments of the invention the produced image can be larger than the field stop in a first direction and the relative position between the produced image and the field stop along the first direction can be changed. Thus due to the change of position in the first direction an optical swivelling of the direction of view is possible in this direction. In particular the field stop can be arranged such that it cannot be displaced along the first direction. In particular the relative position between the produced image and the field stop can be changed by means of the image module only along the first direction. Alternatively the image module can be formed such that the relative position between the produced image and the field stop can be changed both in the first direction and also in a second direction, perpendicular thereto. In this case the produced image is preferably also larger than the field stop in the second direction.

The image module preferably contains at least one movable (preferably steplessly movable) optical element, the position of which fixes the relative position between the produced image and the field stop. As the image module is arranged in the proximal area of the endoscope, there is more room or installation space here, whereby the producibility of the endoscope is made easier.

Furthermore the endoscope according to certain embodiments of the invention can have at the proximal area an actuating element which is coupled to the at least one movable optical element such that the position of the at least one movable optical element can be set by means of the actuating element. The actuating element can for example be a sleeve housed rotatable at the endoscope handle. However, any other form of the actuating element is also possible. The coupling between actuating element and the at least one movable optical element can for example take place via magnets with the result that the endoscope for the lens can also be formed hermetically tight in the proximal area.

The image module can for example have a displaceable (preferably steplessly displaceable) deflecting element. Furthermore it can have a Dove prism which can be displaced (preferably steplessly) perpendicular to its base surface.

The imaging optics of the endoscope according to certain embodiments of the invention are preferably free from movable optical elements in the area of the distal end of the endoscope. Thus a simple miniaturization is achieved.

At the distal end of the endoscope the imaging optics can have a lens which simultaneously seals an opening of the endoscope shaft at the distal end. In particular it can seal this opening hermetically tightly. This lens images the object and thus produces the image. The lens can be formed elongated in a top view. The lens can be produced from glass or plastic. In particular the lens is produced from sapphire glass. The lens can also be formed as a negative lens.

The imaging optics is preferably formed such that the field angle is larger in a first direction than in a second direction, perpendicular thereto. Thus the field angle of the first direction may e.g. lie in the range of from 130°-170° and preferably in the range of from 140°-160°. The field angle in the second direction may lie preferably in the range of from 50°-80° and in particular in the range of from 60°-70°. However, it is also possible that the field angles are the same size in both directions.

The endoscope according to certain embodiments of the invention can, in addition to the lens at the distal end of the endoscope, have at least one illumination opening. For example, ends of optical fibres may lie in this illumination opening. However, it is also possible that a light source, such as e.g. an LED, is arranged directly in these illumination openings.

The endoscope according to certain embodiments of the invention is preferably formed as an endoscope with a rigid endoscope shaft. This is e.g. advantageous in sinuscopy as, when introducing the instrument the operator wishes to look straight ahead into the nose, and upon reaching the area of operation, then wishes to look in another direction of view.

Naturally the endoscope can also be formed such that the endoscope shaft can be bent out at least in one section.

Furthermore the endoscope can have in the proximal area behind the field stop an eyepiece and/or an interface for e.g. a video camera.

With the endoscope according to certain embodiments of the invention the imaging optics can have a proximal final lens which serves as image-expansion lens.

Furthermore, in the distal end area of the endoscope the imaging optics can have an objective and proximally adjoining same an image-transmission lens (which for example contains rod lenses).

The image module can contain at least one optical element which serves to expand the image, to transmit the image and/or to correct distortion.

The endoscope can have further elements known to a person skilled in the art which are necessary for operating the endoscope.

Furthermore an endoscopy method for an endoscope with a variable direction of view is provided, wherein the endoscope has an endoscope shaft and arranged inside the endoscope shaft imaging optics which image an object located before the distal end of the endoscope and produce an image of the object in the proximal area of the endoscope, in which a field stop is arranged, wherein the produced image is produced in a size which is larger than the field stop, and the relative position between the produced image and the field stop is changed in order to change the section visible after the field stop of the produced image and thus the direction of view of the endoscope. In particular the change of the relative position between the produced image and the field stop is carried out steplessly. Furthermore the imaging optics can produce the image as a single continuous image.

The endoscopy method according to certain embodiments of the invention can include further steps which are described in connection with the endoscope according to the invention.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example using the attached drawings which also disclose features essential to the invention.

DETAILED DESCRIPTION

In the following descriptions, the present invention will be explained with reference to example embodiments thereof. However, these example embodiments are not intended to limit the present invention to any specific example, environment, embodiment, applications or particular implementations described in these example embodiments. Therefore, descriptions of these example embodiments are only for purposes of illustration rather than limitation to the invention. It should be appreciated that in the following example embodiments and the attached drawings, elements unrelated to the present invention are omitted from depiction; and dimensional relationships among individual elements in the attached drawings are illustrated only for ease of understanding, but not to limit the actual scale.

Figure 1:
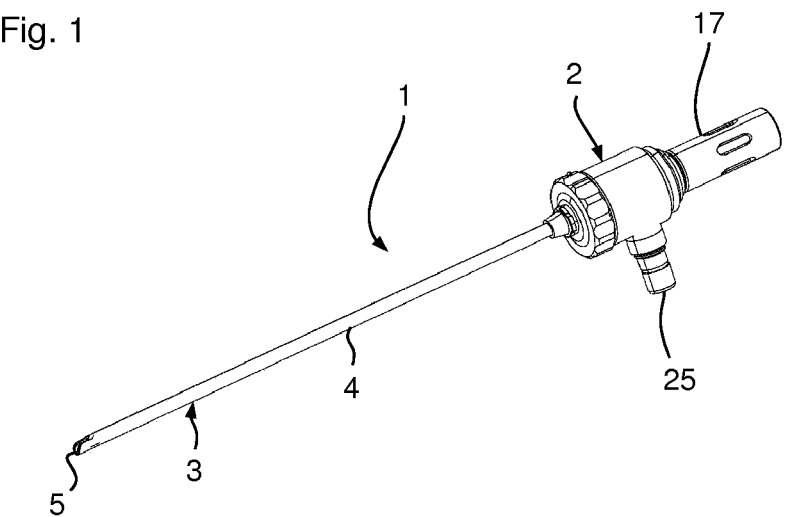
FIG. 1 is a perspective view of a first embodiment of the endoscope according to the invention.

In the embodiment shown in FIG. 1, the endoscope 1 according to the invention is formed as an endoscope 1 with variable direction of view and has a handle 2 as well as an endoscope shaft 3 connected to the handle 2 the casing tube 4 of which can be seen in FIG. 1.

Figure 2:
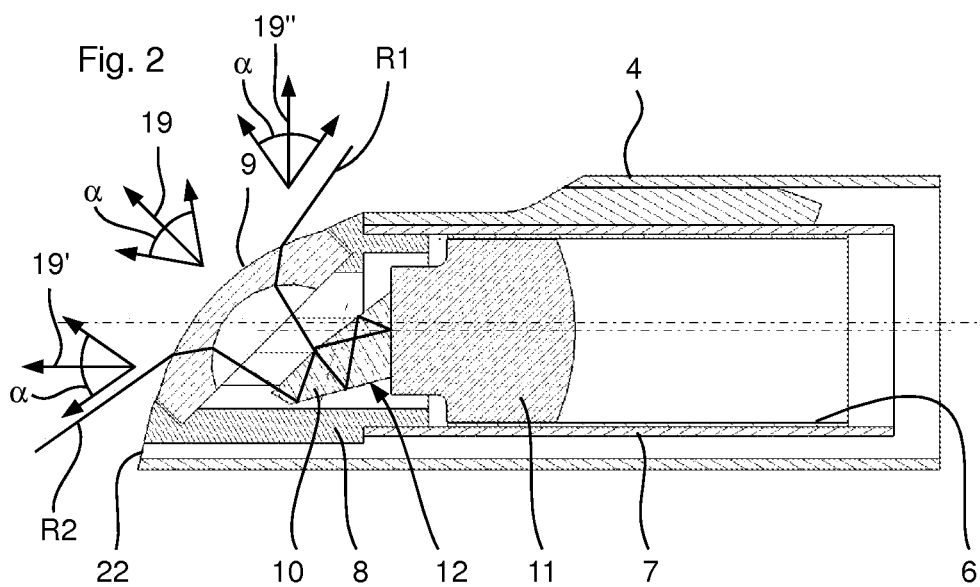
FIG. 2 is an enlarged sectional view of the distal end of the endoscope shaft from FIG. 1.

As can be seen in particular from the enlarged sectional representation of the distal end 5 of the endoscope shaft 3 in FIG. 2, an optics tube 6 is provided which sits in an inner tube 7. The inner tube 7 for its part is arranged inside the casing tube 4. An adapter 8 whose distal end is formed as a mount for a front lens 9 is inserted at the distal end of the inner tube 7.

The front lens 9 which here is formed as a sapphire diverging lens is soldered to the adapter 8 which for its part is soldered to the inner tube with the result that the distal end of the inner tube 7 and therefore also of the optics tube 6 is hermetically tightly sealed.

Figure 3:
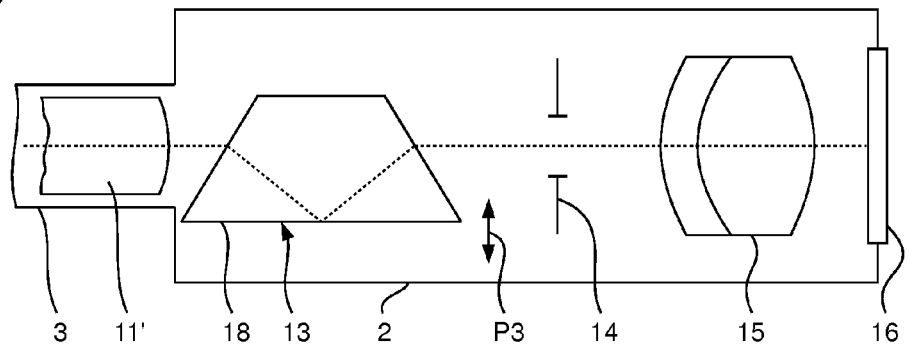
FIG. 3 is an enlarged schematic sectional view of the proximal area of the endoscope 1 from FIG. 1.

A prism element 10, downstream of which is arranged a first objective lens 11 positioned in the optics tube 6, is arranged in the area of the adapter 8. There are further objective lenses and rod lenses, not shown in FIG. 2, in the optics tube 6. The final rod lens 11' which sits at the proximal end of the optics tube 6 is shown in FIG. 3.

The front lens 9, the prism element 10 and the objective and rod lenses 11, 11' are part of imaging optics 12, with which an object before the distal end 5 of the endoscope 1 is imaged such that an image of the object is produced in the proximal area (here in the handle 2) of the endoscope 1.

In order that a user can observe the object, a Dove prism 13 is arranged in the handle 2 followed by a field stop 14 behind which there is arranged an eyepiece 15 in order to provide the user, through an exit window 16, with an enlarged section of the image, as is described in detail below.

Here the imaging optics 12 are formed such that the recordable field angle in the drawing plane of FIG. 2 (or about an axis running perpendicular to the drawing plane) is very large, for example 160°. This is indicated by the drawn-in marginal rays R1, R2 of the field of vision in the drawing plane of FIG. 2. In a direction perpendicular to the drawing plane of FIG. 2 (or about an axis lying in the drawing plane which here encloses an angle of 45° with the longitudinal direction of the endoscope shaft 3) the recordable field angle is smaller, e.g. 70°, with the result that overall an elongated or oblong image B is produced at the proximal end of the endoscope (in the area of the field stop 14) as is represented schematically in FIG. 5. The length of the double-ended arrow P1 corresponds to the larger field angle (here 160°), the length of the double-ended arrow P2 to the smaller field angle (here 70°).

Figure 5:
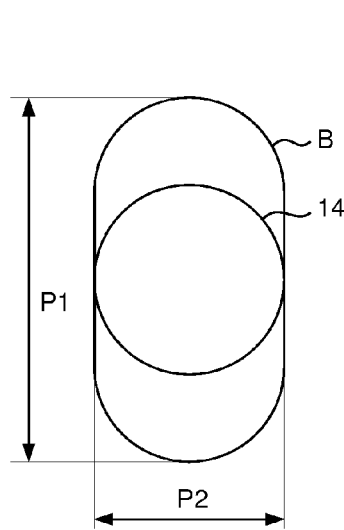
FIG. 5 is a representation explaining the relative position between the image B produced in the proximal area and the field stop 14.

Furthermore the position of the image B relative to the field stop 14 (which is circular here) is represented in FIG. 5. This shows that, for an observer, only a 70° section α (FIG. 1) of the long field angle of 160° (double-ended arrow P1) and the complete short field angle of 70° (double-ended arrow P2) is represented enlarged by means of the eyepiece 15. Below, the long field angle is also called first field angle and the short field angle is also called second field angle. The section represented in FIG. 5 of the first field angle corresponds to a first direction of view 19 of 45° relative to the longitudinal direction of the endoscope shaft 3 as drawn in schematically in FIG. 2.

Figure 4:
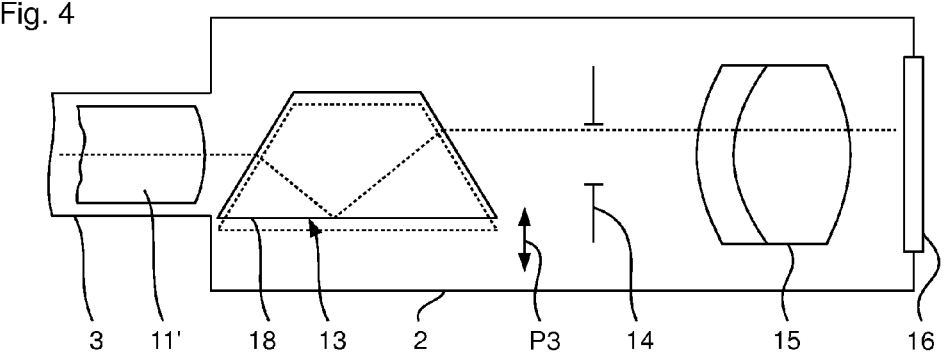
FIG. 4 is the sectional view according to FIG. 3 with changed position of the prism 13.
Figure 6:
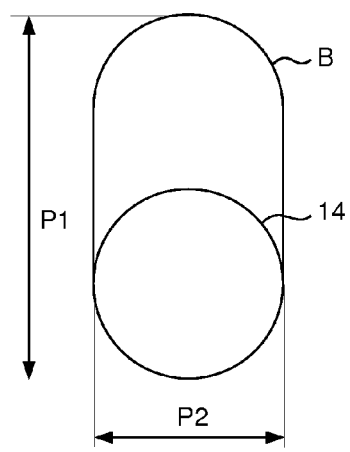
FIG. 6 is a further representation explaining the relative position of the image B produced in the proximal area and the field stop 14.

The Dove prism 13 in the handle 2 can be displaced in the direction of the double-ended arrow P3 (FIG. 3) (perpendicular to the base surface 18 of the Dove prism 13). An upwards displacement of the prism 13 along the direction of the double-ended arrow P3, as is represented in FIG. 4, leads to the image B being likewise displaced upwards relative to the fixed field stop 14 (FIG. 6). For illustration purposes the original position of the Dove prism 13 is represented by a dotted line in FIG. 4.

Due to this change of position of the image B relative to the field stop 14 the section of the image B which corresponds to the direction of view 19' of 0° (FIG. 2) is now shown enlarged by means of the eyepiece 15.

A downwards displacement of the Dove prism 13 from the position in FIG. 3 would lead to an image section which corresponds e.g. to a direction of view 19" of 90° (FIG. 2).

In all adjustable directions of view the represented section α of the first field angle is in each case 70°, with the result that the entire first angle image of −35° to 125° can be represented with the first directions of view of 0°-90°.

A displacement of the image B relative to the field stop 14 thus leads to a change of the first direction of view 19, 19', 19" for the user of the endoscope 1, wherein for this, according to the invention, no movable optical element at all need be provided at the distal end of the endoscope 1. This leads to the advantage that the chosen cross-section of the endoscope shaft or the diameter of the endoscope shaft 3 can be very small (e.g. 4 mm, 3.5 mm, 3.2 mm or smaller) and an endoscope 1 with a variable direction of view is still provided.

An undistorted depiction of the produced image B at the proximal end of the endoscope 1 is difficult to achieve because of the large first field angle P1. However, as only a certain partial area (here the section α) of this first field angle is ever offered to the user on the basis of the field stop 14, it is sufficient, to achieve a desired imaging quality, if the imaging optics 12 are laid out such that the desired imaging quality is present within the visible partial area set by the field stop 14 of the first field angle.

The movable element (prism 13) sits in the proximal area of the endoscope 1 and here in the handle 2. In this area the chosen diameter can be larger because this area is not introduced into the corresponding opening when using the endoscope 1.

To move the Dove prism 13 there can be provided at the proximal end of the endoscope 1 a holder (not shown), in which the Dove prism 13 sits, which can be actuated via an actuating element 17 (FIG. 1) attached externally to the handle 2. For example a magnet coupling can be provided in order to create a hermetically tight inner space in the proximal end for the Dove prism 13, the field stop 14 and the eyepiece 15. In this case e.g. the exit window 16 is hermetically tightly connected to the proximal end of the endoscope 2 (e.g. by soldering). Naturally all other types of mechanical coupling between actuating element 17 and holder are also possible for the Dove prism 13 such as e.g. a direct mechanical coupling if a hermetical tightness is not desired in the area of the Dove prism.

In particular the actuating element 17 can be housed rotatable and/or displaceable in axial direction at the handle 2 in order to bring about the desired movement of the Dove prism 13.

The actuating element 17, the Dove prism 13 as well as their mechanical coupling form an image module with which the relative position of the produced image B and field stop 14 can be changed and set in order to set the direction of view 19, 19' of the endoscope 1.

Figure 7:
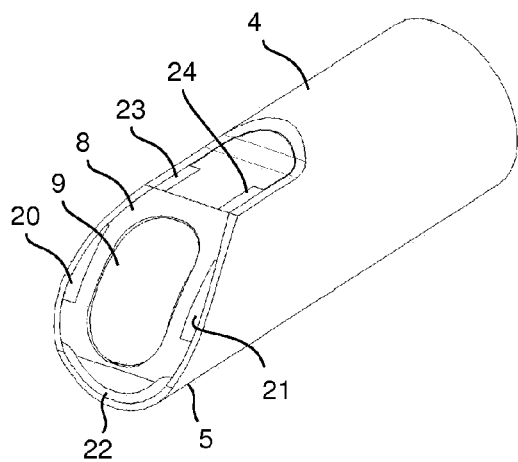
FIG. 7 is a perspective enlarged representation of the distal end of the endoscope shaft according to FIG. 1.

The front lens 9, as can be seen from the perspective representation of FIG. 7, also has an elongated shape because of the asymmetrical image B. This is furthermore advantageous as two outlets 20 and 21 can be provided alongside the front lens 9, an outlet 22 below the front lens 9 and two outlets 23 and 24 above the front lens 9. These outlets 20-24 are e.g. allocated to channels which run between the inner tube 7 and the casing tube 4 along the longitudinal direction of the endoscope shaft 3. There can be arranged in these channels e.g. optical fibres (not shown) which can be impacted at the handle 2 by light via an optical fibre connection 25 (FIG. 1), with the result that via the outlets 20 to 24 they can emit the light for illuminating an object lying in front of the distal end 5 of the endoscope 1. Naturally other illumination means such as e.g. LEDs can also be provided in the areas 20-24.

Expansion optics, not shown, (e.g. a corresponding expansion lens) can be arranged between the final rod lenses 11' and the prism 13 shown in FIGS. 3 and 4. Additionally, or alternatively, the final rod lens 11' can itself be formed as an expansion lens or as expansion optics. Thus the image, produced in the proximal end of the endoscope 1, of the object becomes larger, whereby the following mechanical and optical parts can also be formed larger, which simplifies their production. As the proximal area of the endoscope 1 and thus the handle 2 are involved, an enlargement is not disadvantageous here.

Figure 8:
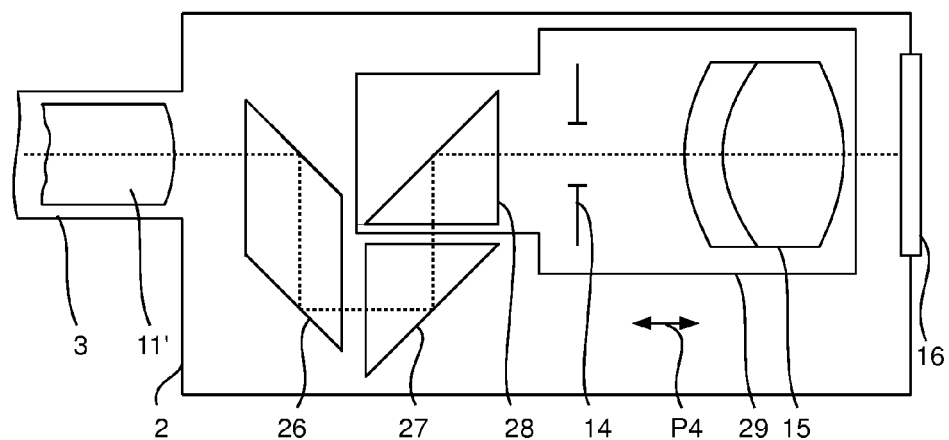
FIG. 8 is a schematic sectional representation of the proximal area of the endoscope according to the invention according to a further embodiment.
Figure 9:
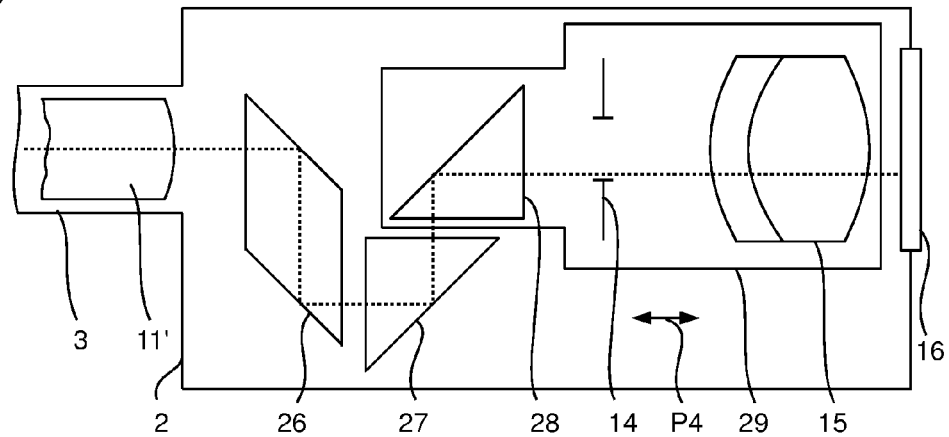
FIG. 9 is the schematic sectional representation according to FIG. 8 with a changed position of the displacement unit 29 compared with FIG. 8.

A variant of the endoscope according to the invention according to FIGS. 1 to 7 is shown in FIGS. 8 and 9, wherein only the differences are described below. Thus in the area of the proximal end three prisms 26-28 are provided instead of the Dove prism 13. Of these three prisms the prisms 26 and 27 are fixed prisms whose position cannot be changed and the prism 28 is a movable prism 28. The prism 28 sits, together with the field stop 14 and the eyepiece 15, in a displacement unit 29 which can be displaced along the longitudinal direction of the endoscope shaft 2 relative to the fixed prisms 26 and 27 as is illustrated by the double-ended arrow P4 in FIGS. 8 and 9. For this, the displacement unit 29 can be coupled to the actuating element 17 (e.g. in the same or similar manner as the coupling of actuating element 17 and Dove prism 13 according to the embodiment of FIGS. 1 to 7). The relative position between the image B and the field stop 14 depending on the displacement position of the displacement unit 29 is set. Therefore, in the same way as the embodiment described in connection with FIGS. 1-7, the corresponding section of the image B and thus the first direction of view can be chosen which is offered to the observer via the eyepiece 15.

Figure 10:
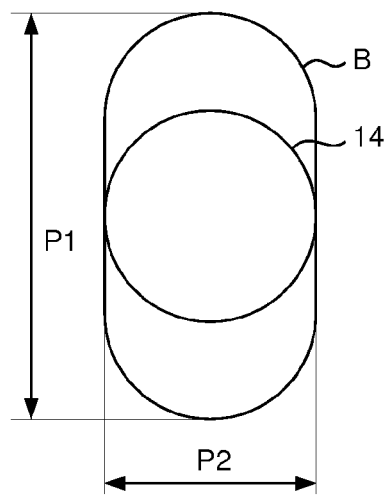
FIG. 10 is a representation of the relative position of the image B produced in the proximal area and of the field stop 14.
Figure 11:
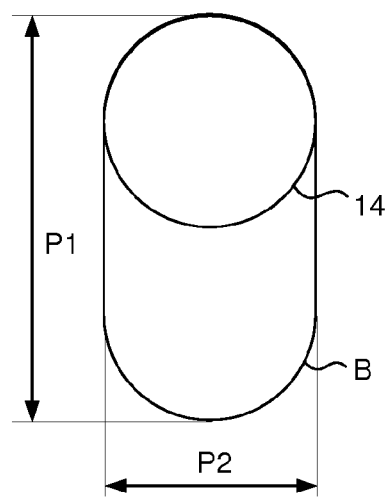
FIG. 11 is a further representation of the relative position of the produced image B and of the field stop 14.

Thus e.g. the displacement unit 29 can be displaced to the right, as is shown in FIG. 9, compared with its position in FIG. 8. This then leads to the image B being displaced downwards along the first field angle P1 relative to the field stop 14, as is schematically represented in FIGS. 10 and 11, wherein FIG. 10 shows the position of the image B relative to the field stop 14 according to the position of the displacement unit 29 from FIG. 8 and FIG. 11 the position of the image B relative to the field stop 14 according to the position of the displacement unit 29 in FIG. 9. The relative position in FIG. 11 between the image B and the field stop 14 corresponds to a first direction of view 19" of 90°, as is drawn in FIG. 2.

In this embodiment a movement of optical elements in the proximal end of the endoscope 1 in longitudinal direction of the endoscope shaft 3 thus leads to the desired change or setting of the first direction of view 19, 19', 19". The displacement unit 29, the actuating element 17 and their mechanical coupling here form an image module for setting the direction of view.

Naturally, other first directions of view can also be set with the described embodiments than the first directions of view 19, 19' and 19" described by way of example. The specific first direction of view always depends on the position of the produced image B relative to the field stop 14 in the proximal end of the endoscope.

The produced image in the area of the field stop 14 can be the image offered to the user or can be an intermediate image which is used for presentation to the user.

Also, in the same way as in the embodiment according to FIGS. 3 and 4, with the embodiment described in connection with FIGS. 8 and 9 expansion optics can be arranged between the final rod lens 11' and the prism 26. Furthermore, likewise additionally, or alternatively, the final rod lens 11' can itself be formed as expansion optics or expansion lens. Furthermore, additionally or alternatively in the proximal area of the endoscope in all embodiments described at least one further optical element can be arranged which e.g. serves to improve image quality (for example correct distortion) or to change the image size. With the embodiment shown in connection with FIGS. 8 and 9 optics can be arranged e.g. between the two prisms 26 and 27 which serve to make possible problem-free image transmission by means of the prisms 26 and 28 despite the relative length of the glass paths under the circumstances.

With the endoscope 1 according to the above-described embodiments the endoscope shaft 3, together with all of the optical elements, can be housed rotatable vis-à-vis the handle 2 in the proximal end of the endoscope 1 with the result that, by rotating the endoscope shaft 3, the direction of view can be changed into the second direction which corresponds to the direction according to double-headed arrow P2.

The description thus far has assumed that the image B is displaced only along a first direction (double-headed arrow P1 in FIGS. 5 and 6 as well as in FIGS. 10 and 11) relative to the field stop 14 and the field stop 14 covers the complete image B in the second direction (double-headed arrow P2).

Figure 12:
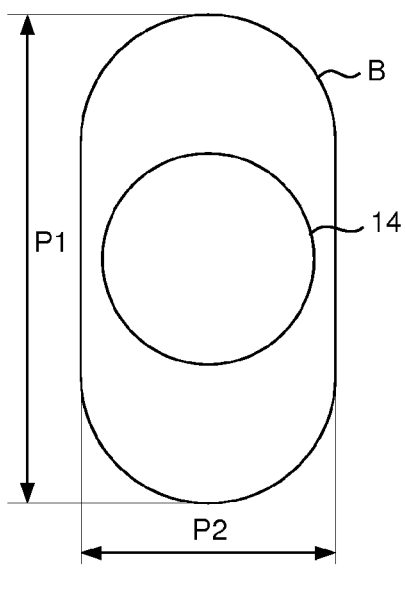
FIG. 12 is a representation of the position of the field stop 14 relative to the produced image in the proximal area according to a further embodiment.
Figure 13:
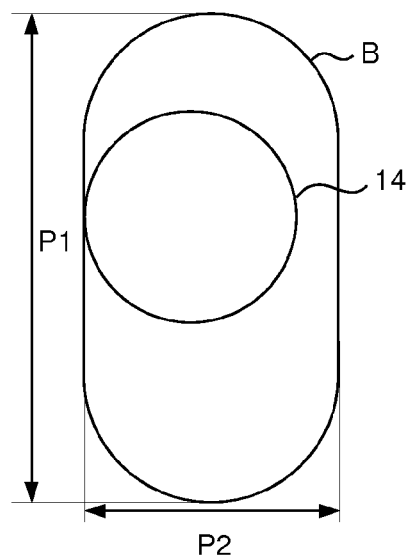
FIG. 13 is a representation of the relative position between the image B and the field stop 14 explaining the further embodiment.

Naturally the endoscope 1 can also be formed such that the image B also covers a greater expansion in the second direction (double-headed arrow P2) than the field stop 14, as illustrated schematically in FIG. 12. The image B can be displaced in both directions relative to the field stop 14 by a corresponding formation of the image module, which corresponds to a change of first and second direction of view. Thus a change of the represented section of the whole field angle of the imaging optics 12 in different directions is then possible with the result that the user can set the desired direction of view without movable parts having to be provided at the distal end 5 of the endoscope 1.

Thus e.g. with the embodiment according to FIGS. 3 and 4 there can be arranged behind the Dove prism 13 and in front of the field stop 14 a second Dove prism which is arranged rotated by 90° about the longitudinal axis of the endoscope 2 vis-à-vis the first Dove prism 13. The second Dove prism can be moved back and forth in a direction perpendicular to the drawing plane, wherein this movement leads to a displacement of the image B in the second direction of view (double-headed arrow P2). Thus the desired direction of view can be fixed inside the image B.

The field stop 14 is always described here as a stop with a circular contour. Naturally any other shape of contour is also possible such as e.g. a square or any other polygonal shape.

The produced image B can be oblong but does not have to assume this shape. Any other shape is possible in principle, such as e.g. a circle.

With the endoscope according to the invention 1 the imaging optics 12 between the lens 9 and the prism element 10 can also have at least one further optical element (such as e.g. a lens).

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An endoscope with a variable direction of view, comprising:
    an endoscope shaft; and
    imaging optics arranged inside the endoscope shaft which image an object located before the distal end of the endoscope and produce an image of the object in the proximal area of the endoscope in which a field stop is arranged,
    wherein the produced image is larger than the field stop and in the proximal area of the endoscope an image module is arranged with which the relative position between the produced image and the field stop can be changed for changing the section of the produced image visible after the field stop in order to change the direction of view of the endoscope, wherein the image module brings about a stepless change of the relative position between the produced image and the field stop, wherein the image module includes a Dove prism which can be displaced perpendicular to a base surface of the Dove prism, wherein the imaging optics produce a single coherent image, and wherein the produced image is the image offered to a user of the endoscope or an intermediate image which is used for presentation to the user.

2. The endoscope according to claim 1, wherein the produced image is larger in a first direction than the field stop and in that the relative position between the produced image and the field stop along the first direction can be changed.

3. The endoscope according to claim 2, wherein the field stop cannot be displaced along the first direction.

4. The endoscope according to claim 1, wherein the position of the Dove prism sets the relative position between the produced image and the field stop.

5. The endoscope according to claim 4, wherein at the proximal area the endoscope has an actuating element which is coupled to the Dove prism with the result that the position of the at least one movable optical element can be set by means of the actuating element.

6. The endoscope according to claim 1, wherein the imaging optics is free from movable optical elements in the area of the distal end of the endoscope.

7. The endoscope according to claim 1, wherein the imaging optics have, at the distal end of the endoscope, a lens which simultaneously seals an opening of the endoscope shaft at the distal end.

8. The endoscope according to claim 7, wherein the lens is formed elongated in a top view.

9. The endoscope according to claim 7, wherein the lens is formed as a negative lens.

10. The endoscope according to claim 7, wherein in addition to the lens at the distal end of the endoscope there is at least one illumination opening.

* * * * *